(12) United States Patent
Eckstein et al.

(10) Patent No.: US 8,846,372 B2
(45) Date of Patent: Sep. 30, 2014

(54) IDENTIFICATION OF BACTERIAL SPECIES AND SUBSPECIES USING LIPIDS

(75) Inventors: Torsten Manfred Eckstein, Fort Collins, CO (US); Julia Mitsue Inamine Eckstein, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 543 days.

(21) Appl. No.: 12/959,248

(22) Filed: Dec. 2, 2010

(65) Prior Publication Data

US 2011/0086384 A1 Apr. 14, 2011

Related U.S. Application Data

(62) Division of application No. 11/934,057, filed on Nov. 1, 2007, now abandoned.

(60) Provisional application No. 60/856,118, filed on Nov. 2, 2006.

(51) Int. Cl.
*C12N 1/20* (2006.01)
*C12Q 1/04* (2006.01)

(52) U.S. Cl.
USPC .................... 435/253.1; 435/34; 435/252.1

(58) Field of Classification Search
None
See application file for complete search history.

(56) References Cited

U.S. PATENT DOCUMENTS

| | | | |
|---|---|---|---|
| 4,965,202 A | 10/1990 | Haley et al. | |
| 5,059,527 A * | 10/1991 | White et al. | 435/29 |
| 6,310,007 B1 | 10/2001 | Kuo et al. | |
| 6,833,249 B2 | 12/2004 | Khanuja et al. | |

OTHER PUBLICATIONS

Leavell et al. "Fatty Acid Analysis Tool (FAAT): An FT-ICR MS Lipid Analysis Algorithm", Anal. Chem. 2006, vol. 78, pp. 5497-5503.*

Ecktein et al.("A Major Cell Wall Lipopeptide of Mycobacterium avium subspecies paratuberculosis". The Journal of Biological Chemistry, vol. 281, No. 8, pp. 5209-5215, (Feb. 24, 2006).*
Eckstein et al. "Lipidomics of Mycobacterium avium subspecies paratuberculosis: Characterization of MAP-specific cell envelope lipids". Abstracts of the 105th General Meeting of American Society for Microbiology, Jun. 8, 2005, p. 577.*
Basile et al. "Pathogenic bacteria: their detection and differentiation by rapid lipid profiling with pyrolysis mass spectrometry". Trends in Analytical Chemistry. 1998, vol. 17, No. 2, pp. 95-108.*
Singh et al. "Characterization of lipid pattern of Mycobacterium paratuberculosis isolates from goats and sheep". Indian Journal of Animal Science, Sep. 2000, 70 (9): 899-903.*
Torsten M. Eckstein et al., A Major Cell Wall Lipopeptide of Mycobacterium Avium Subspecies Paratuberculosis, J. Biol. Chem. 281, p. 1-18 (2006).
Phung, Le Van et al., "Cellular Lipid and Fatty Acid Compositions of Burkholderia Pseudomallei Strains Isolated From Humans and Enviroment in Viet Nam," Microbiol. Immunol. (1995), 39 (2), pp. 105-116.
Yabuuchi et al., "Burkholderia Uboniae Sp. Nov., L-Arabinose-assimilating but Different from Burkholderia Thailandensis and Burkholderia Vietnamiensis," Microbiol. Immunol. (2000), 44 (4), pp. 307-317.

* cited by examiner

*Primary Examiner* — Vera Afremova
(74) *Attorney, Agent, or Firm* — Samuel M. Freund; Cochran Freund & Young LLC

(57) ABSTRACT

The use of free, extractable lipids found in bacteria for identification of bacterial species and subspecies is described. Bacteria have been found to differ sufficiently in their extracted lipid compositions to effect identification using thin layer chromatographic techniques. *Burkholderia pseudomallei*, *Burkholderia thailandensis*, and *Burkholderia mallei* have been distinguished in this manner. Lipopeptides specific to *Mycobacterium avium* subspecies *paratuberculosis*, but not to the closely related bacterium *Mycobacterium avium* subspecies *avium* have also been used as a basis for bacterial subspecies identification using mass spectrometry and seroreactivity. Mass spectrometric analysis of total bacterial lipids of *Burkholderia pseudomallei*, *Burkholderia thailandensis*, and *Burkholderia mallei*, and mass spectrometric analysis of total bacterial lipids for *Mycobacterium avium* subspecies *paratuberculosis* and *Mycobacterium avium* subspecies *avium*, without further lipid separation, has shown that species and subspecies of bacteria may be identified using such analysis.

1 Claim, 7 Drawing Sheets

FIG. 5

IDENTIFICATION OF BACTERIAL SPECIES AND SUBSPECIES USING LIPIDS

RELATED CASES

The present patent application is a divisional of U.S. patent application Ser. No. 11/934,057, filed on Nov. 1, 2007 now abandoned, which claims the benefit of Provisional Patent Application Ser. No. 60/856,118 filed on Nov. 2, 2006 and entitled "Major Cell Wall Lipopepetide Of *Mycobacterium Avium* Subspecies" by Torsten M. Eckstein et al., which applications are hereby incorporated by reference herein for all that they disclose and teach.

STATEMENT REGARDING FEDERAL RIGHTS

This invention was made with government support under Contract Numbers: P01-AI-046393; P01-AI-057836; R01-AI-033706; R01-AI-051283; R01-AI-053796; U54-AI-065357; and R37-AI-018357, awarded by the National Institute of Allergy and Infectious Diseases of the U.S. National Institutes of Health to Colorado State University; Contract Number 2004-35605-14243 USDA/CSREES, awarded by the U.S. Department of Agriculture Coop State Research and Extension Service to Colorado State University; and Contract Number Q6286224112 from the Johne's Disease Integrated Program (JDIP) awarded as a subcontract from the University of Minnesota to Colorado State University, awarded to the University of Minnesota by the U.S. Department of Agriculture (CREESE-NRI). The government has certain rights in the invention.

FIELD OF THE INVENTION

The present invention relates generally to the identification of bacterial species and, more particularly, to the use of lipids found in bacteria for the identification of bacterial species and subspecies.

BACKGROUND OF THE INVENTION

Bacteria are often detected in the context of the disease they cause, but few infectious diseases are sufficiently specific that a physician can treat them directly. However, even for those diseases proof is necessary. The most common identification method is by direct culture of the specific pathogen, which is for many pathogens the "gold-standard" of detection and determination of the infectious disease. The second most used method for defining an infectious disease and its causative agent is indirect identification through antibody detection either to the whole bacterium, crude extracts, fractions of the pathogen, or single molecules. Indirect identification methods have the disadvantage of identifying other bacteria instead of the actual pathogen due to cross-reactivity of the extracts, fraction, or whole bacteria. Therefore, such tests only provide a first step for identification. Of particular interest are tests that focus on single molecules such as proteins. However, such tests have not been proven to be species-, subspecies-, or type-specific, and thus, share the same disadvantages as exist for whole extracts or fractions of whole bacteria (that is, cross-reactivity, as an example).

All bacteria consist of nucleic acids (RNA, DNA), proteins, saccharides, and lipids. Although these molecules may provide information for identifying bacterial species, subspecies and types, the most commonly used are nucleic acids and proteins. Comparative methods for chromosomal DNA and proteins have been developed to distinguish these species, but these molecules are not generally useful because of their low efficiency in specific techniques (DNA in PCR amplification, or cross-reactivity in hybridization techniques), or due to the large number of similar molecules within the proteome (several thousand molecules may have to be compared as a result of separation techniques having poor efficiency). There are fewer molecules belonging to the group of saccharides and lipids. However, methods for successful separation of saccharides are not yet available.

Despite these shortcomings, DNA sequences are presently used as amplification templates for identification of the bacterial species, subspecies, and types. Such DNA sequences are principally repetitive sequences for increasing the positive outcome of the PCR amplification procedure. Since these tests are multi-factorial, false-negative data that cannot be proven to be correct may result, and the tests do not have a "backup" target to verify a negative result.

The small subunit (SSU) rRNA has been found to be useful for distinguishing species from one another with a high degree of certainty. However, this marker can define an unknown strain of a species only if there is a certain taxonomical distance between this species and another. Classification/taxonomy defines the differences between bacteria. To determine a classification or taxonomic relationship, at least three bacteria are required, whereas to distinguish bacteria a minimum of two bacteria are required. Closely related species (for example, *Mycobacterium avium* and *Mycobacterium intracellulare*) cannot be distinguished with certainty by this method alone, and use of the SSU 16S rRNA sequence cannot distinguish bacterial subspecies and types since these subspecies have the same sequence. Furthermore, determining the SSU rRNA sequence requires multifactorial amplification by polymerase chain reaction.

Additional biological tests including DNA G+C content and chemotaxonomic methods, such as analysis of prominent cell wall molecules, may be required to obtain high confidence for species identification. Other investigations use the fatty acid composition to determine species. However, fatty acids must be generated by chemical reactions to release them from lipid molecules. Identification of bacterial subspecies and types may require other biochemical, enzymatic, and/or physiological methods, including information as to where those bacterial subspecies and types were obtained.

Species identification begins with isolation and growth of the bacterium either in-vitro or, if not possible, in-vivo, followed by extraction of chromosomal DNA and PCR amplification of the SSU 16S rRNA. However, in many situations the original sequence is not known and amplification processes cannot be performed. To reduce the number of possibilities, multiple standard biochemical, enzymatic, and physiological tests allow the determination of the bacterial species with high certainty for most bacterial species. However, to determine bacterial subspecies and types additional microbiological aspects must be considered, such as growth time, growth supplements, colony morphology, as examples.

SUMMARY OF THE INVENTION

Accordingly, it is an object of the present invention to provide a method for identifying bacterial species.

Another object of the invention is to provide a method for identifying bacterial subspecies.

Yet another object of the present invention is to provide a method for identifying bacterial species without the use of DNA amplification procedures.

Still another object of the invention is to provide a method for identifying bacterial species with a reduced number of false negatives.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the method for identifying a single bacterial species containing at least one extractable lipid, hereof, includes the steps of: extracting at least one bacterial lipid using an organic solvent; and identifying at least one lipid by its polarity.

In another aspect of the invention, and in accordance with its objects and purposes, the method for identifying a single bacterial subspecies containing at least one extractable lipid, hereof, includes the steps of: extracting at least one bacterial lipid using an organic solvent; and identifying at least one lipid by its polarity.

In still another aspect of the invention, and in accordance with its objects an purposes, the method for identifying a single bacterial species containing at least one extractable lipid, hereof, includes the steps of: extracting at least one bacterial lipid using an organic solvent; and identifying at least one lipid by its molecular weight.

In yet another aspect of the invention, and in accordance with its objects and purposes, the method for identifying a single bacterial subspecies containing at least one extractable lipid, hereof, includes the steps of: extracting at least one bacterial lipid using an organic solvent; and identifying at least one lipid by its molecular weight.

In a further aspect of the invention, and in accordance with its objects and purposes, the method for identifying a single bacterial subspecies containing at least one extractable lipid, hereof, includes the steps of: extracting at least one bacterial lipid using an organic solvent; and identifying at least one lipid by its immunological properties.

Benefits and advantages of the present invention include, but are not limited to, providing a method for identifying bacterial species and subspecies without the use of amplification procedures, and with a minimum of false negatives.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 2A illustrates a two-dimensional thin layer chromatography plate for lipids extracted from *Mycobacterium avium* subspecies *paratuberculosis* in non-polar solvent system E of TABLE 1 hereof, while FIG. 2B illustrates a two-dimensional thin layer chromatography plate for lipids extracted from *Mycobacterium avium* subspecies *hominissuis* in the same solvent system.

FIG. 5 shows matrix-assisted laser desorption ionization time-of-flight mass spectra of total bacterial lipids for *Burkholderia thailandensis*, *Burkholderia mallei* (middle); and *Burkholderia pseudomallei* (bottom).

DETAILED DESCRIPTION OF THE INVENTION

Figure 1:
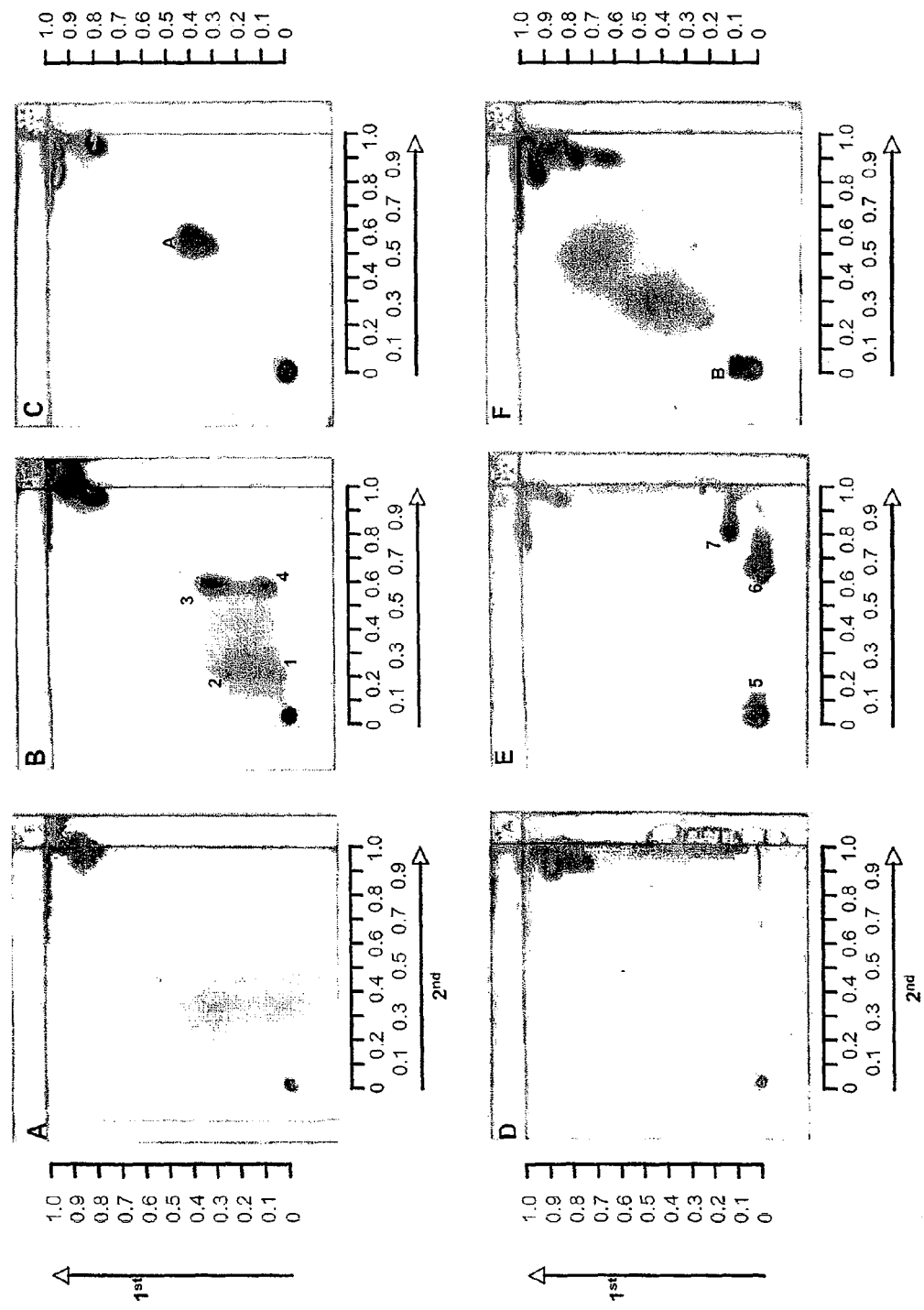
FIGS. 1A-1F are thin layer chromatograms of *Burkholderia thailandensis* (A and D), *B. pseudomallei* (B and E), and *B. mallei* (C and F) for non-polar solvent system E (A, B, and C) and polar solvent system A (D, E and F) of TABLE 1 hereof.

Briefly, the present invention includes the use of free, extractable lipids found in bacteria for identification of bacterial species and subspecies. In what follows the term "lipid" refers to molecules that are soluble in non-polar (organic) solvents, but are barely or insoluble in water. Lipids are therefore termed lipophilic, which refers to the ability of a chemical compound to dissolve in fats, oils, lipids, and non-polar solvents or mixtures of non-polar and polar solvents. Further, the term "bacterial lipids" refers to lipid molecules generated by bacteria and found either within the cell itself or as molecules released into the environment surrounding the bacteria, known as supernatant or culture filtrate, when the bacteria are grown in a liquid medium.

The data presented below are from lipids from bacterial cells and not from the culture filtrates. However, lipids may be extracted from the culture filtrate which is initially lipid free, and are important for bacterial identification.

Lipids have a variety of polarities and compositions, and examining lipid profiles are shown to characterize bacterial species, subspecies, and types, and to distinguish them from other bacterial species, and subspecies (a type in some bacteria is similar to a subspecies; in others, a type is a sub-subspecies.). Additionally, some bacterial species and groups include more lipid moieties than the average bacterium, making lipids valuable for directly identifying pathogens by detecting antibodies from the host of the infectious disease.

Lipids are molecules that can be extracted from cell samples of bacterial species, subspecies and types using various organic solvents (chloroform, methanol, petroleum ether, and acetone, as examples) and mixtures of these species with water, acids, and/or bases, as examples. The Folch wash using chloroform/methanol/water in the ratios 6:4:1 by volume may be employed as a purification step. Additional fractionation may be useful for enhancing the presence of certain lipids. Lipid molecules may then be separated by two-dimensional thin layer chromatography using a solvent system which spans the polarity range for these molecules. As will be set forth below, five mixtures of solvents were employed for this step. This is usually defined as a range for which the liquids having the strongest polarity will migrate away from the loading location, and for the least polar system, none of the lipids will reach the final solvent front. Lipids may be visualized using known standard general or specific spraying methods or by UV-light detection.

Thus, lipids obtained from different bacterial species, subspecies, and types may be separated by their polarities and, as will be described in more detail below, it is possible to distinguish bacterial species, subspecies and types of closely related bacteria, by comparing their lipid profiles with those for other species.

In accordance with one embodiment of the present invention, specific lipid molecules have been found in certain bacteria, but not in related species, subspecies and types. The determination of the chemical structure and/or the characteristic profiles for each of those molecules generated using mass spectrometric analyses and the ionization fragmentation pattern of these molecules will definitively identify the bacterial species, subspecies, and type. Thus, the knowledge of the specific lipid profile, the knowledge of the chemical structure of species-specific and subspecies-specific lipids, and the knowledge of their ionization and fragmentation patterns in mass spectrometric analyses provide a method for identifying a bacterium in a mixture of bacteria, in an unknown sample, cells, and/or tissues by analyzing the lipid extracts.

More specifically, lipids may be extracted from lyophilized cells using chloroform/methanol (2:1 by volume), in contact with (30 ml/g) dried cells for several hours at 55° C. for 3 h. After centrifugation at about 3500 rpm for 5 min., the supernatant may be separated from cell debris by transfer to a new tube. Additional lipid extraction may be performed on dried debris with chloroform/methanol/water (10:10:3 by volume) at room temperature for several hours (up to over night). Debris may be separated from the supernatant by centrifugation at approximately 3500 rpm for 5 min. and transferred to the first supernatant. Supernatant may be dried under constant flow of nitrogen gas. A Folch wash may be performed on the crude lipid extract to remove potential salt contamination, if necessary. The Folch wash may be performed by adding about 6 ml of chloroform/methanol solution (2:1 by volume) and approximately 1 ml of water to the dried crude lipid extract with vigorous mixing. The organic layer (bottom) may be transferred to a new tube and dried using flowing nitrogen gas. Lipids may be extracted from culture filtrates as described for lyophilized bacterial cells.

Lipid extraction from wet cells may be performed with slight modification. Extraction from wet cells may be performed with chloroform/methanol (1:1 by volume) (7 ml/1 ml wet cells) at room temperature for about 3 h. After centrifugation at about 3500 rpm for approximately 5 min., the supernatant may be transferred to a new tube. Dried debris may be further extracted with chloroform/methanol (2:1 by volume) (30 ml/g dried debris) at 55° C. for about 3 h. Supernatant may be transferred to the tube containing the first lipid extraction supernatant after centrifugation at about 3500 rpm for approximately 5 min., and dried under a constant flow of nitrogen gas. If necessary, a Folch wash can be performed as described above.

Lipid separation may be accomplished using two-dimensional thin layer chromatography (2-D TLC) on silica-based gels/plates using five different solvent systems spanning a range of polarity (see TABLE 1). The most polar system should allow all lipids to move away from the loading location, and the least polar system should not have lipids moving with the solvent front. Ideally, 200 µg total lipids will be spotted onto a 2-D TLC; however, as little as 20 µg total lipids may be sufficient. After separation, lipid spots may be visualized by spraying with a general stain (for example, 10% $CuSO_4$ in 8% $H_3PO_4$), followed by heating until the spots appear. More specific stains may be used to detect specific lipid groups such as glycolipids, lipids containing free amino groups, phospholipids and others. Approximately 400 µg (the equivalent of a single colony) is generally required for a single analysis.

TABLE 1

2D-TLC solvent systems used for lipid analysis.

| Polarity | Name | 1st Dimension | 2nd Dimension |
|---|---|---|---|
| Polar ↓ | B | Chloroform/methanol/water (60:30:6) | Chloroform/acetic acid/methanol/water (40:25:3:6) |
| Apolar | A | Chloroform/methanol/water (100:14:0.8) | Chloroform/acetone/methanol/water (50:60:2.5:3) |
|  | E | Chloroform/methanol (96:4) | Toluene/acetone (80:20) |
|  | C | Petroleum-ether/acetone (92:8) | Toluene/acetone (95:1) |
|  | D | Petroleum-ether/ethyl acetate (98:2) | Petroleum-ether/acetone (98:2) |

Thus, the lipid profile of a bacterial species, subspecies and type is used to distinguish a specific bacterial species or subspecies from another bacterial species or subspecies (see EXAMPLE 1 below).

Lipids specific to a bacterial species, subspecies and type are used to distinguish a particular bacterial species or subspecies from others by direct detection using mass spectrometry (see EXAMPLE 2 below).

Some bacterial lipids are useful as diagnostic markers; recent studies have demonstrated that bacterial lipids are processed by CD1+ bearing cells. This permits lipids to be recognized as specific antigens by CD1 restricted T cells, and targeted as T cell vaccine candidates or used to develop cellular-based immuno-detection strategies with lipids for diagnostic purposes. Lipids also serve as B cell antigens that generate antibodies within the host. Immunogenic lipids specific to a bacterial species or subspecies are indirectly used for bacterial detection by methods such as ELISA (see EXAMPLE 3 below).

Mass spectra of total bacterial lipids have proven valuable in the identification of bacterial species and subspecies (see EXAMPLE 4 below).

Having generally described the invention, the following EXAMPLES provide additional details:

EXAMPLE 1

Identification of Related Bacterial Species (*Burkholderia pseudomallei* Versus *B. thailandensis* and *B. mallei*):

*Burkholderia pseudomallei* is the causative agent of melioidosis, a chronic disease in humans. The disease manifests itself in two distinct forms: an acute infection or as an acute bloodstream infection, and as a chronic infection. In chronic or recurrent melioidosis, the lungs are most commonly affected. Mortality is high—up to 86%. This disease is very common in South-East Asia and Northern Australia. A closely related non-pathogenic bacterium, *Burkholderia thailandensis*, is commonly found in the environment. Another related bacterial pathogen is *Burkholderia mallei*, the causative agent of glanders, mainly a disease in horses, but can also affect humans. The standard method for laboratory diagnosis of melioidosis is the isolation of the pathogen. This generally takes at least 3 days. Humans with severe infections, especially those with septicemia, often die before results become available. In addition, for patients with affected visceral organs (liver, lung, and spleen) it is almost impossible to obtain material for culturing the pathogen. The detection of antibodies in the sera to species-specific antigens is helpful in the diagnosis of melioidosis. The most common serological test used in endemic regions, the indirect hemaglutination assay (IHA) using crude bacterial antigen-coated erythrocytes, is difficult to perform and often has poor specificity. Newer ELISA tests use purer *B. pseudomallei* antigen preparations (for example, the 200 kDa antigen, LPS, crude culture filtrate (CCF) containing a 30 kDa antigen, and recombinant Bps-1 antigen) with demonstrated increased sensitivities and specificities up to 80%. However, for routine diagnosis these methodologies have not been proven to be superior to the IHA test.

Reference will now be made in detail to the present embodiments of the invention, examples of which are illustrated in the accompanying drawings. Identical numbers are used to represent identical lipids on the two-dimensional chromatograms. Turning now to FIG. 1, thin layer chromatograms of *Burkholderia thailandensis* (A and D), *B. pseudomallei* (B and E), and *B. mallei* (C and F) are illustrated for non-polar solvent system E (A, B, and C) and polar solvent system A (D, E and F) described in TABLE 1 hereof.

The three related bacterial species can readily be distinguished from one another by comparing the lipid profiles in the two solvent systems utilized, as may be observed in TABLES 2-5 which show the Rf values of each lipid within the given system (where the Rf value is the percentage of the distance the lipid has moved when compared to the movement of the solvent front representing 100% or unity), and FIGS. 1A-1F.

TABLE 2

*B. pseudomallei*, FIG. 1B, Solvent System E

| Lipid | $1^{st}$ dimension | $2^{nd}$ dimension |
|---|---|---|
| 1 | 0.12 | 0.24 |
| 2 | 0.29 | 0.24 |
| 3 | 0.15 | 0.61 |
| 4 | 0.39 | 0.62 |

TABLE 3

*B. mallei*, FIG. 1C, Solvent System E

| Lipid | $1^{st}$ dimension | $2^{nd}$ dimension |
|---|---|---|
| A | 0.45 | 0.62 |

TABLE 4

*B. pseudomallei*, FIG. 1E, Solvent System A

| Lipid | $1^{st}$ dimension | $2^{nd}$ dimension |
|---|---|---|
| 5 | 0.05 | 0.12 |
| 6 | 0.05 | 0.7 |
| 7 | 0.17 | 0.9 |

TABLE 5

*B. mallei*, FIG. 1F, Solvent System A

| Lipid | $1^{st}$ dimension | $2^{nd}$ dimension |
|---|---|---|
| B | 0.12 | 0.06 |

The thin layer chromatograms for *B. thailandensis* illustrate that there are no lipids dissolved in either solvent system E (FIG. 1A) or solvent system A (FIG. 1D).

Clearly, *B. mallei* presents one lipid spot in each solvent system, while *B. pseudomallei* presents 4 readily observable lipids and 3 readily observable lipids in the solvent systems E and A, respectively. Lipid spots can be distinguished if their edges differ by about 2%.

EXAMPLE 2

Identification of Related Bacterial Subspecies (*Mycobacterium avium* Subspecies *paratuberculosis* (MAP) Versus *M. avium* Subsp. *avium* (MAA) and *M. avium* Subsp. *hominissuis* (MAH)) by Lipid Profiling and by Mass Spectroscopy:

A. Lipid Profiling:

*Mycobacterium avium* subspecies *paratuberculosis* is the causative agent of Johne's disease, a chronic enteritis in ruminants (cattle, sheep), while *M. avium* subsp. *hominissuis* and *M. avium* subsp. *avium* are closely related subspecies of the same species *M. avium* that are often found in the environment.

*M. avium* subsp. *avium* (MAA) and *M. avium* subsp. *hominissuis* (MAH) are environmental opportunistic pathogen that cause respiratory diseases in the general population which can be distinguished only by the presence or absence of IS901. Environmental mycobacteria are ubiquitous in municipal as well as natural waters, and the primary source of human infection is thought to be water. MAP can be distinguished from MAA/MAH by the presence of IS900 (although similar elements are present in MAA/MAH and other mycobacteria, and it is now being questioned whether this is a true MAP-specific IS element), and by its growth characteristics (MAP has the slowest growth rate, with a generation time of 22-26 h compared to 10-12 h for MAA/MAH, and requires the siderophore mycobactin to grow). Potential transmission mechanisms from cattle to humans have been identified including dairy products, meat, and contaminated water sources. If there is an association between MAP and Crohn's disease, and if dairy products (particularly milk) and beef are involved in transmission, the human health concerns may be considerable.

The bacterial culturing of MAP from feces is still considered the "gold standard" for the diagnosis of infected animals. However, this procedure is time consuming (up to 16 weeks) and expensive. Most of the attention is going now to the detection of serum antibodies against MAP products and these are the bases of commercially available test kits. However, these tests suffer from very modest sensitivity. The overall specificities for four tests for bovine *paratuberculosis* were higher than 95% but the sensitivities were only 38.4, 26.6, 58.8, and 43.4% for the complement fixation test, the agarose gel immunodiffusion test, an ELISA test from Allied Laboratories, and an ELISA test from CSL, Limited, respectively. This is a disadvantage for those tests since their specificities are less than that for the gold standard of fecal cultures.

Figure 2:
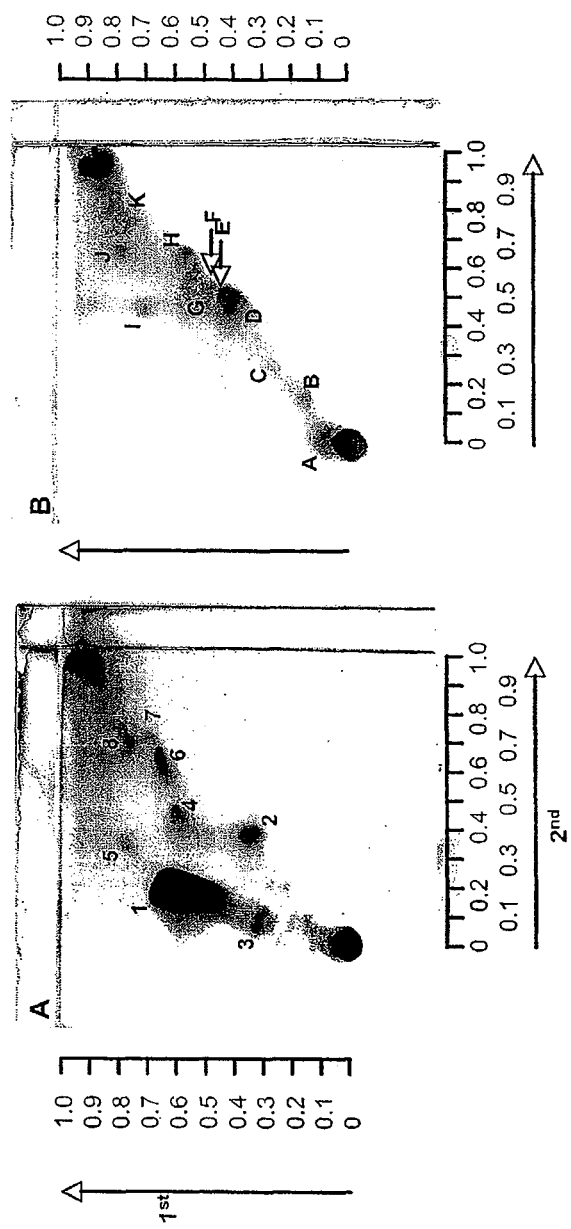

As stated, the subspecies MAP and MAA/MAH can be presently distinguished only by growth rate, colony morphology, and growth supplements within a sample (blood, feces, tissue, saliva, milk, as examples). FIG. 2A illustrates a two-dimensional thin layer chromatography plate for lipids extracted from *Mycobacterium avium* subspecies *paratuberculosis* in non-polar solvent system E, while FIG. 2B illustrates a two-dimensional thin layer chromatography plate for lipids extracted from *Mycobacterium avium* subspecies *hominissuis* in the same solvent system. By analyzing the extracted lipid profile using one of the five solvent systems described above, *M. avium* subsp. *paratuberculosis* can clearly be distinguished from *M. avium* subsp. *hominissuis* by lipids 1 to 3, and by the presence or absence of lipid 1, respectively. See also TABLES 6 and 7 which show the Rf values for the various lipids.

TABLE 6

*Mycobacterium avium* subspecies *paratuberculosis*, In Solvent System 3

| Lipid | 1$^{st}$ dimension | 2$^{nd}$ dimension |
|---|---|---|
| 1 | 0.7 | 0.27 |
| 2 | 0.38 | 0.42 |
| 3 | 0.35 | 0.12 |
| 4 | 0.63 | 0.5 |
| 5 | 0.8 | 0.38 |
| 6 | 0.68 | 0.69 |
| 7 | 0.7 | 0.74 |
| 8 | 0.8 | 0.72 |

TABLE 7

*Mycobacterium avium* subspecies *hominissuis*, In Solvent System 3

| Lipid | 1$^{st}$ dimension | 2$^{nd}$ dimension |
|---|---|---|
| A | 0.11 | 0 |
| B | 0.19 | 0.18 |
| C | 0.28 | 0.3 |
| D | 0.43 | 0.52 |
| E | 0.46 | 0.54 |
| F | 0.5 | 0.54 |
| G | 0.59 | 0.6 |
| H | 0.06 | 0.68 |
| I | 0.72 | 0.48 |
| J | 0.81 | 0.69 |
| K | 0.77 | 0.78 |

As stated above, lipid spots can be distinguished if their edges differ by about 2%.

B. Identification of *Mycobacterium avium* Subsp. *paratuberculosis* from a Putative Sample by Direct Detection of Specific Lipids Using Mass Spectrometry:

The lipid, Para-LP-01 was selected for further characterization because it is a major cell wall-associated lipid, was well-isolated when the total lipids were separated by 2D-TLC using an apolar solvent system, and was present only in MAP bacterial species.

MAP strain K-10 is a bovine isolate grown on Middlebrook 7H11 agar plates supplemented with 10% OADC (oleic acid, albumin, dextrose, catalase) and Mycobactin J (2 µg/ml). After 12 weeks of growth at 37° C., cells were harvested by scraping colonies from the plates into PBS, pH 7.0, and centrifuging at 3,500 rpm for 30 min. Cell pellets were then lyophilized.

Total lipids were extracted from lyophilized MAP cells in accordance with the procedure identified above, and separated by 2-dimensional (2-D) thin layer chromatography (TLC) on aluminum backed silica 60 F$_{254}$ gel plates using chloroform/methanol (96:4) in the first dimension and toluene/acetone (80:20) in the second dimension. Plates were sprayed with 10% copper sulfate in 8% phosphoric acid, and the lipids visualized by heating. Total lipids were further analyzed by differential spraying of the plates to detect carbohydrates (using α-naphthol), free amino groups (using ninhydrin), and phosphates (using ceric ammonium molybdate) after heating. Several lipids were found to be specific to MAP; two, in particular were found in significant quantities: Para-LP-01 (lipid 1 in FIG. 2A) and Para-LP-02 (lipid 2 in FIG. 2A).

Para-LP-01 was purified by preparative TLC. It was first scraped from plates run in chloroform/methanol 96:4 by volume, and then the lipopeptide was subjected to a second preparative TLC purification using the solvent system of toluene/acetone 80:20 by volume. For extraction from the silica, chloroform/methanol (2:1 by volume) solution was used in an incubation at 4° C. overnight. Extracts were dried under nitrogen and purified by Folch wash, and the organic layer was transferred to a fresh tube. The dried organic layer was suspended in chloroform/methanol (2:1) at a concentration of 10 mg/ml. Amino acids were identified following the hydrolysis of 100 µg of lipid Para-LP-01 with 6N HCl overnight at 110° C. by gas chromatography coupled to mass spectrometry (GC/MS). Specifically, the analyte was introduced into a DB-5 column (10 m×0.18 mm internal diameter, 0.18 µm film thickness) on a trace gas chromatograph connected to a mass detector at an initial temperature of 60° C. for 1 min., increasing to 130° C. at 30° C./min and finally to 280° C. at 5° C./min. Fatty acid analysis was conducted by hydrolyzing the Para-LP-01 with 6 N HCl overnight at 110° C. followed by 3N HCl in methanol at 85° C. for 16 h. The sample was treated with TRI-SIL reagent for 20 min. at 70° C. Analysis of the trimethylsilylated compounds was performed by GC/MS using the same column and temperature program described for amino acids. To determine the enantiometric form of amino acids an (R)-(−)-2-butanol and an (S)-(+)-2-butanol derivatization was performed, and the resulting O-butyl, N-heptafluorobutyryl amino acid butyl derivatives were analyzed by GC/MS as described above.

GC/MS analysis of the derivatized amino acids yielded three major components corresponding to standards for alanine, isoleucine, and phenylalanine, respectively. A minor component that correlated with a valine standard was also identified. Details of the gas chromatography/mass spectroscopy and NMR analyses of the Para-LP-01 may be found in "A Major Cell Wall Lipopeptide of *Mycobacterium avium* subspecies *paratuberculosis*," by Torsten M. Eckstein et al., J. Biol. Chem. 281, pp. 5209-5215 (2006), the teachings of which are hereby incorporated by reference herein.

The enantiomeric forms of the amino acids were determined by analyzing the O-butyl, N-heptafluorobutyryl amino acid butyl derivatives. GC analysis demonstrated that the amino acids alanine, valine, and isoleucine were present only in the L-configuration whereas phenylalanine was detected in both the L- and D-configurations.

Positive ion FAB-MS (Cesium-ion Fast Atom Bombardment Mass Spectrometry) analysis of Para-LP-01 identified the masses of alanine (methyl ester), phenylalanine, and isoleucine, along with seven fatty acyl chains linked to a pentapeptide core. MALDI-TOF (Matrix-Assisted Laser Desorption Ionization Time-Of-Flight) analysis identified seven saturated fatty acyl chains linked to the peptide core: hexadecanoic acid, heptadecanoic acid, octadecanoic acid, nonadecanoic acid, eicosanoic acid, heneicosanoic acid, and docosanoic acid.

The above analyses indicate that Para-LP-01 is a lipopeptide complex or family in which a pentapeptide core is attached to a series of saturated fatty acids dominated by C20. From component analysis, the calculated mass (890.6) differed from the major ion identified by FAB-MS (918.6) by 28 amu. The nature of this difference was examined by $^1$H NMR and $^1$H-$^{13}$C NMR demonstrated the presence of two phenylalanines, one alanine, one isoleucine, and one valine, and it also provided strong evidence for a saturated fatty acid. In addition, the calculated difference in the mass of the lipopeptide of 28 amu could be accounted for by N-linked and O-linked methyl groups. Further structural analysis of the native lipopeptide and its deuteromethylated derivative using MALDI-TOF indicated that four deuteromethyl groups were incorporated into the lipopeptide, and that the replacement of one methyl group by a deuteromethyl group, which had to come from an ester, was consistent with a methyl ester at the carboxyl group. Since five amide bonds were expected according to the data reported above, the MALDI-TOF data showed that one amide bond was naturally N-methylated.

Figure 3:
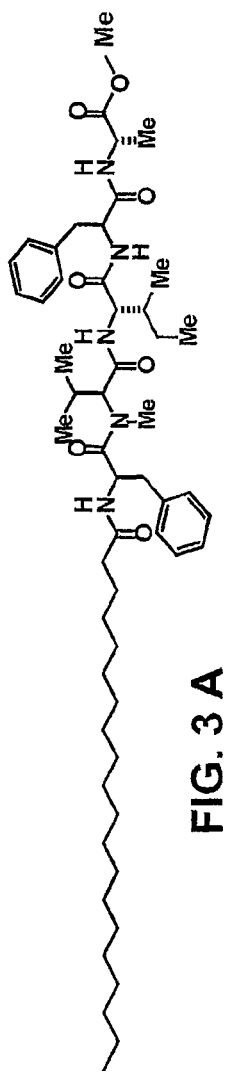
FIG. 3A shows the structure identified for the lipopeptide, Para-LP-01 (lipid 1 of *M. avium* subsp. *paratuberculosis* [(N-terminal to C-terminal) C20:0 fatty acyl D-Phe-N-Me-L-Val-L-Ile-L-Phe-L-Ala methyl ester]), while the characteristic ion thereof, 940.6, is clearly visible in the mass spectrum shown in FIG. 3B.
Figure 3:
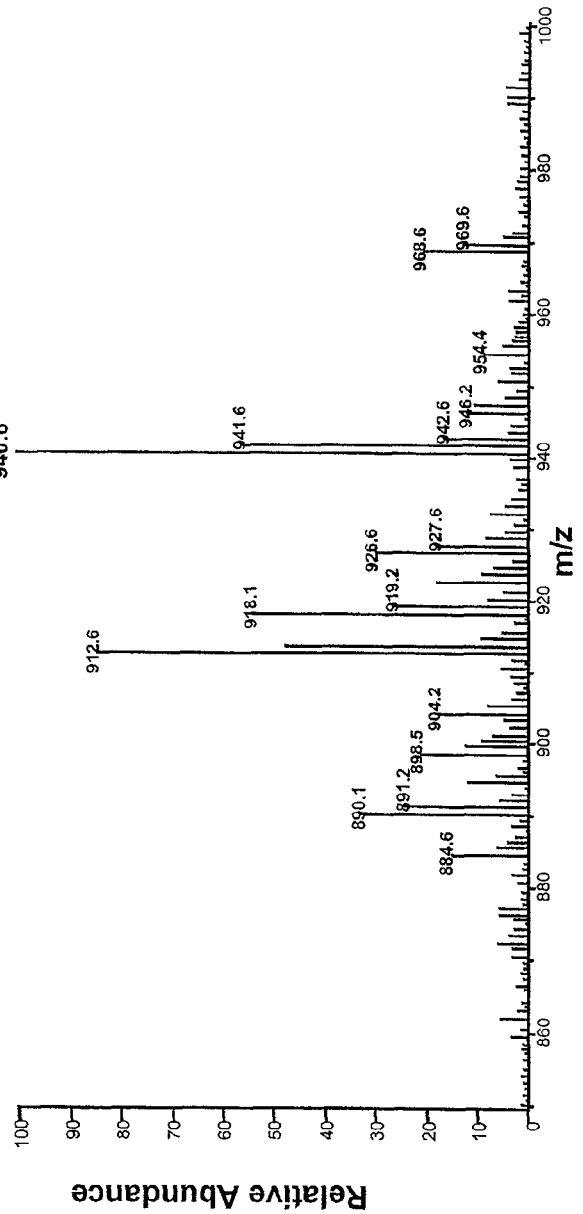

ES/MS (Electrospray Mass Spectrometry) was used to determine the location of the N-methylation, and demonstrated that the peptide sequence is comprised of N-Me-valine-isoleucine-phenylalanine-alanine methyl ester. Thus, the structure of the lipopeptide consists of pentapeptide Phe-N-Me-L-Val-L-Ile-Phe-L-Ala methyl ester N-linked to a C20 fatty acid that was identified as the major fatty acid. As stated above, amino acid analysis revealed the presence of both the D- and L-isomers of phenylalanine. In silico analyses of the MAP genome revealed two single genes and three gene clusters encoding putative peptide synthetases. The one most likely to be involved in the biosynthesis of the lipopeptide Para-LP-01, MAP1420, consists of five modules, one for each of the five amino acids. The first module contains the motif for the incorporation of an epimerized amino acid as the first amino acid. The second module contains the motif for N-methylation of a non-epimerized amino acid, while the final three modules would also direct the incorporation of L-amino acids. In addition, the first module exhibits a high degree of homology (63% identity; 75% similarity) to the first module of the pstA gene product in MAA that is responsible for the incorporation of a D-phenylalanine into the lipopeptide core of the highly immunogenic glycopeptidolipids. Thus, the structure of Para-LP-01 was determined to be: C20:0 fatty acyl D-Phe-N-Me-L-Val-L-Ile-L-Phe-L-Ala methyl ester (N-terminal to C-terminal), as is shown in FIG. 3A hereof.

With the identification of lipids from *M. avium* subsp. *paratuberculosis* that are specific to this subspecies and the identification of the chemical structure of those lipids (here lipid 1 from FIG. 2), the presence of this subspecies has been identified by mass spectrometry of the total lipid extract of the sample. The characteristic ion of lipid 1 (940.6) can be clearly identified in FIG. 3B. Further fragmentation of this ion illustrates that the ion 940.6 belongs to lipid 1 of *M. avium* subsp. *paratuberculosis* since those fragmentation ions and ions of yet additional subfragmentation require a specific structure from lipid 1 of *M. avium* subsp. *paratuberculosis*.

Figure 4A:
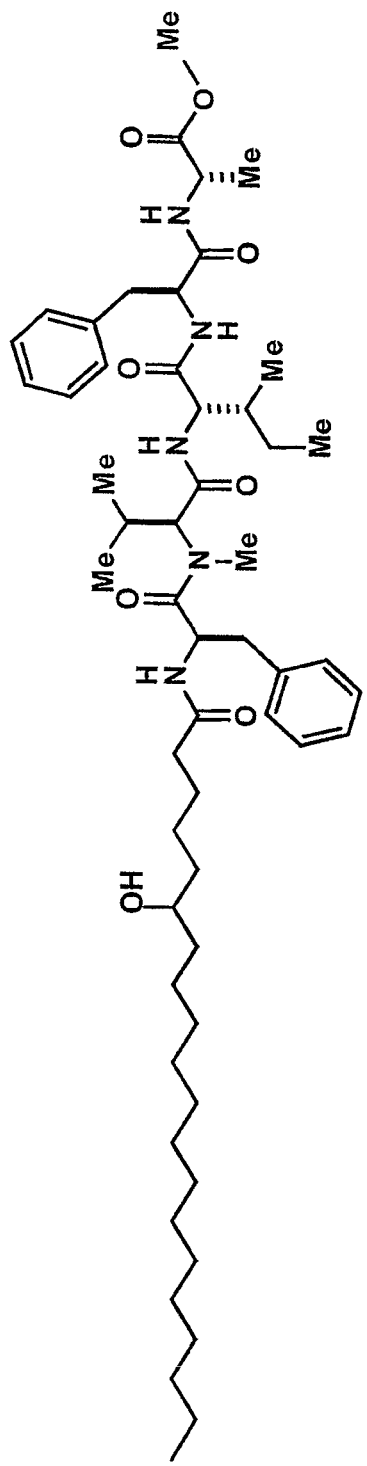
FIG. 4A shows the structure identified for the lipopeptide Para-LP-02 (lipid 2 of *M. avium* subsp. *paratuberculosis* [(N-terminal to C-terminal) 6-hydroxyeicosanoic fatty acyl D-Phe-N-Me-L-Val-L-Ile-L-Phe-L-Ala methyl ester]), while the characteristic ion thereof, 956.7, is visible in the mass spectrum shown in FIG. 4B.
Figure 4:
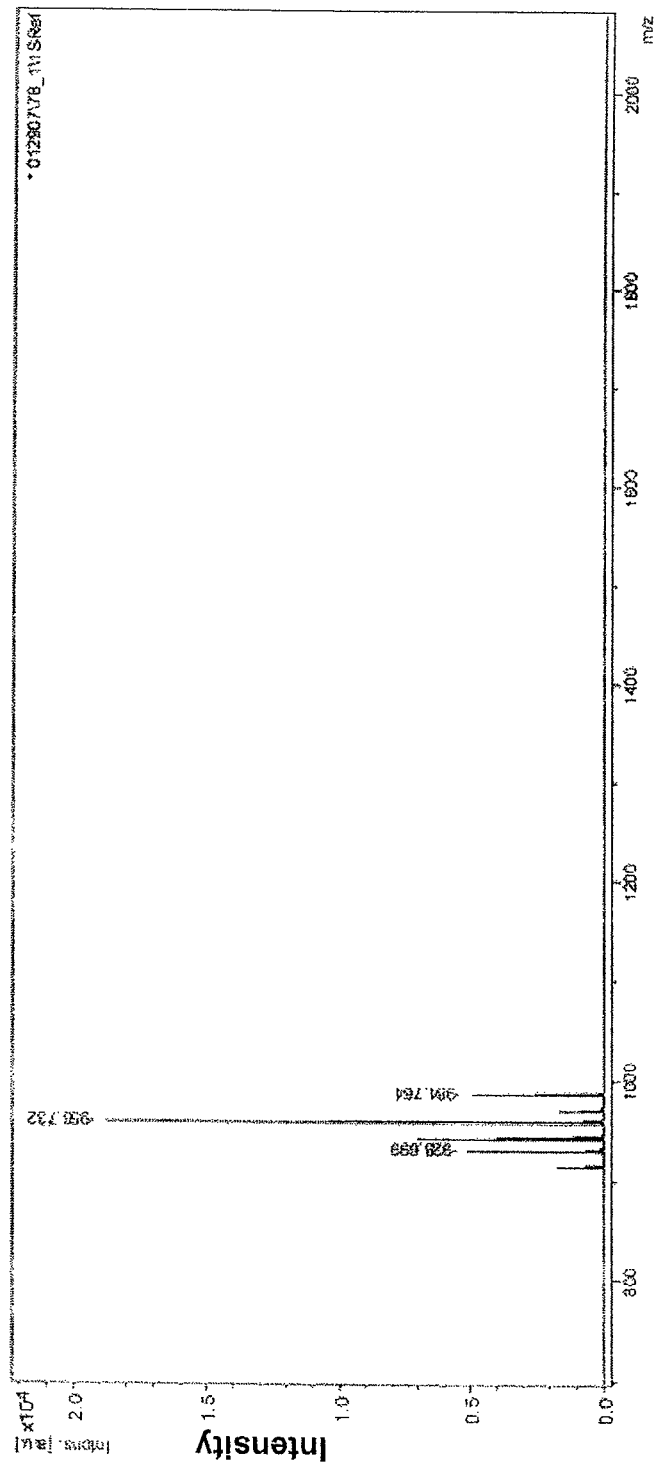

A similar analysis shows that the lipopeptide Para-LP-02 has the structure shown in FIG. 4A (lipid 2 of *M. avium* subsp. *paratuberculosis* [(N-terminal to C-terminal) 6-hydroxyeicosanoic fatty acyl D-Phe-N-Me-L-Val-L-Ile-L-Phe-L-Ala methyl ester]), while the characteristic ion thereof, 956.7, is visible in FIG. 4B. Para-LP-02 differs from Para-LP-01 by its fatty acyl chain.

EXAMPLE 3

Host Immune Response to Mycobacterial Lipids:
A. Microtiter Plate ELISA:

Immunogenic species, such as members of the *M. avium* complex, exhibit seroreactivity of the glycopeptidolipids, which are immunogenic molecules in the outer part of the cell envelope. Structurally, they consist of a lipopeptide core made out of a tetrapeptide (three amino acids and one amino alcohol) that is N-linked to a mono- or di-unsaturated long fatty acid. O-linked to this core molecule are mono- and oligosaccharides, which may be further modified (for example, by methylation or acylation). These sugar moieties are responsible for the 28 different serovars within this complex. One characteristic of MAP is the absence of those highly immunogenic glycopeptidolipids due to gene decay. Several Studies have focused on the seroreactivities of lipid moieties of mycobacteria, but also lipoglycans (lipoarabinomannan, lipomannan) and oligosaccharides. The seroreactivities of single lipid molecules: phenolic glycolipids (PGLs), 2,3 diacyl trehalose, and polar lipooligosaccharides (LOS) in patients with tuberculosis have been examined, and only the LOS antigen appears to be a potential marker for detecting the development of tuberculosis in HIV patients. However, in another study PGLs were used in combination with trehalosedimycolate (TDM) and sulfolipids (SLs) to analyze the seroreactivity with sera from patients with tuberculosis. This study reported a sensitivity of 81.1% with specificity of 95.7%.

Enzyme-linked immunosorbent assay (ELISA) was performed at room temperature in a 96-well microtiter plate with bovine sera and tested by a *Mycobacterium paratuberculosis* Test Kit for Johne's disease. All sera and antibody dilutions were made with 10% fetal bovine serum in phosphate buffered saline (PBS; pH 7.4). Para-LP-01 was suspended in hexane, sonicated for 3 min., and 1 µg was loaded into each well and air-dried. Blocking was performed with 200 µl of blocking buffer (3% bovine serum albumin (BSA) in PBS, pH 7.4) for 1 h. After removing the blocking solution, serial dilutions of the bovine sera (200 µl) were added to duplicate wells and incubated for 2 h. Wells were washed five times with 200 µl blocking buffer and then 100 µl of the secondary antibody (sheep anti-bovine IgG coupled to horseradish peroxidase diluted 1:2000 was added and incubated for 2 h. The wells were washed five times with 200 µl PBS (pH 7.4) before 100 µl of 3,3',5,5'-tetramethylbenzidine was added. After 5 min., the reaction was stopped using 100 µl of 2N sulfuric acid and the $OD_{450}$ was determined using a plate reader.

Para-LP-02 was found to cross-react with antibodies generated in chicken towards Para-LP-01. Both lipids were found to react with bovine sera from cattle with Johne's disease.
B. TLC-ELISA:

Lipids may be identified as immunogenic and thus as diagnostic markers by thin layer chromatography enzyme-linked immunosorbent assay (TLC-ELISA). Lipids may be separated using two-dimensional thin layer chromatography (2D-TLC) in many solvent systems (see Table 1, hereof, for examples). After lipid separation, the plates may be dried at room temperature by constant or intermittent airflow, as examples. Dry TLC plates containing separated lipids may be blocked with 0.25% bovine serum albumin (BSA) in phosphate buffered saline (PBS) (pH7.4) for one hour. After removal of the blocking solution, the plates may be incubated with specific antibodies or a host serum of interest (in 10% fetal bovine serum, if necessary) overnight at 4° C. or at room temperature for a few hours. After several wash steps with PBS, plates may be incubated with secondary antibodies specific for the primary antibodies of interest or the host serum for about 1 h. The plates may then be subjected to several washes using PBS. Color detection may be performed by contacting the plates with TMB (3,3',5,5'-tetramethylbenzidine) for at least 5 min., or until blue spots appear on a light blue background. The color detection step is then stopped by washing the plates several times with PBS. Plates may be dried overnight for further image analyses. Dark blue spots turn yellow to whitish color overnight, but may remain as dark blue spots. Background color may change to light or darker green. The TLC plates may be further analyzed by additional staining for detection of all lipids separated by this solvent system. Briefly, dried plates may quickly be dampened in PBS and quickly incubated in 2N sulfuric acid. The color of the plate will turn yellow. Lipid spots may be visualized by careful heating of the plates until spots appear.

In summary, two major nonpolar lipids, termed Para-LP-01 and Para-LP-02, were identified to be present only in MAP but not in MAA. These lipids were purified and subjected to structural analyses. The fatty acids associated with the Para-LP-01 lipid were saturated and ranged from C16 to C22, while the fatty acids associated with the Para-LP-02 lipid were hydroxylated at the 6 position of the saturated fatty acids ranging in size from C16 to C22.

Para-LP-01 is a major lipid in the cell wall and is likely a major component of the outer part of the cell envelope, just as the glycopeptidolipids (GPLs) of MAA are surface exposed. Although MAP is technically a member of the *M. avium* complex, it lacks GPLs and is missing some of the genes responsible for their biosynthesis. Para-LP-01 and Para-LP-02 consist of a peptide core with five amino acids that are distinct from those found in the GPL core. Furthermore, an additional modification of an amino acid (N-methylation) was identified within the Para-LP-01 and Para-LP-02 that is not found in the GPLs. Finding an N-methylated valine in the lipopeptide structure of Para-LP-01 and of Para-LP-02 was unexpected.

Many lipid components of the cell envelope of mycobacteria demonstrate seroreactivity. The best examples are the highly immunogenic GPLs of the *M. avium* complex localized to the outer part of the cell envelope. Although many studies have demonstrated the seroreactivities of different lipid molecules none have identified a lipopeptide as the target molecule. Thus, the present MAP-specific molecules are the first described mycobacterial lipopeptides exhibiting biological activity through its seroreactivity with sera from cattle with Johne's disease.

EXAMPLE 4

Mass Spectra of Total Bacterial Lipids:

Total lipids of the cells of single bacterial species or subspecies or of the culture filtrate the bacteria were grown in were extracted as described above. Mass spectra of the total bacterial lipids were performed by MALDI-TOF using DHB (dihydrobenzoate) as the matrix for co-crystallization. Ions appear as a mass over charge plus sodium in general, or with hydrogen.

Figure 5:
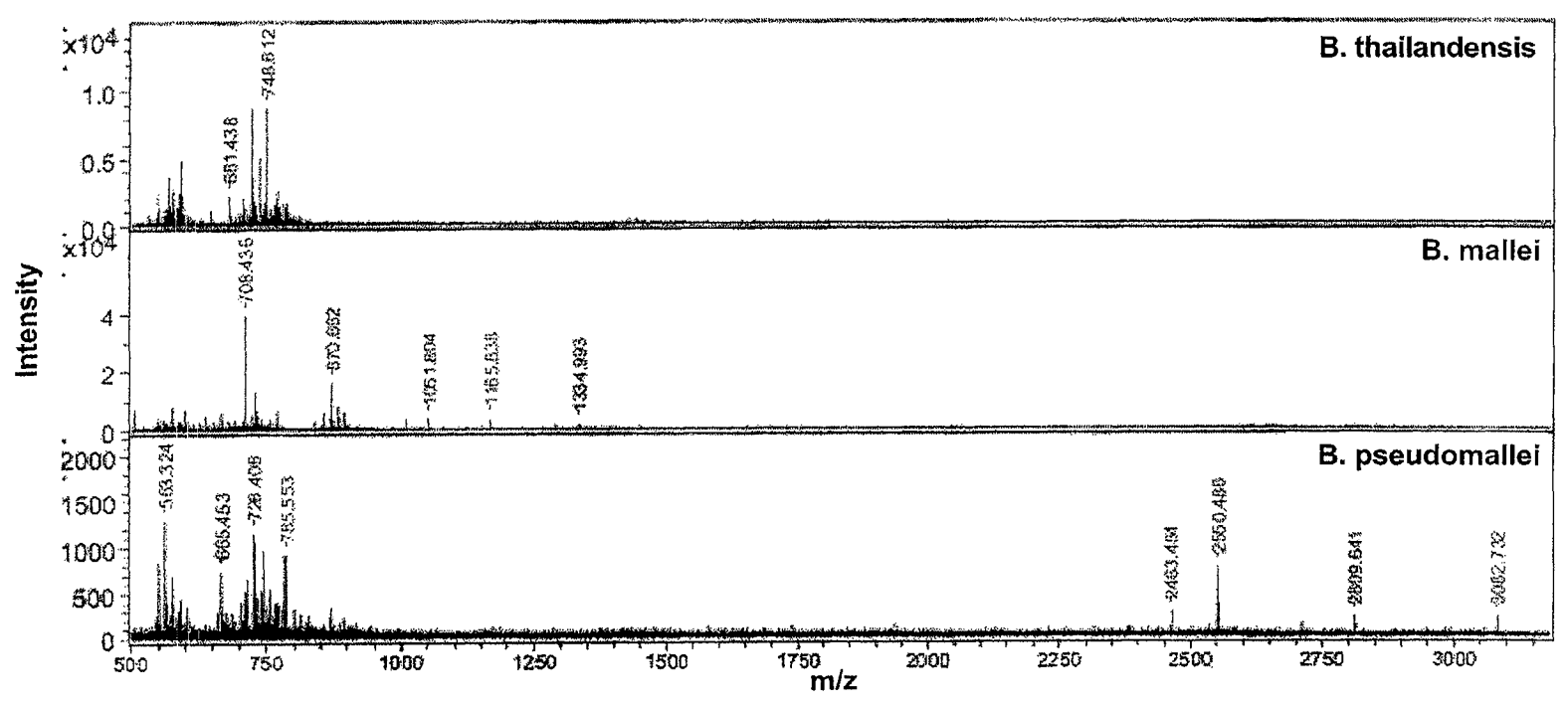

FIG. 5 shows MALDI-TOF mass spectra of total bacterial lipids for *Burkholderia thailandensis, Burkholderia mallei* (middle); and *Burkholderia pseudomallei* (bottom). The three bacterial species can clearly be identified using the mass spectra thereof.

Figure 6:
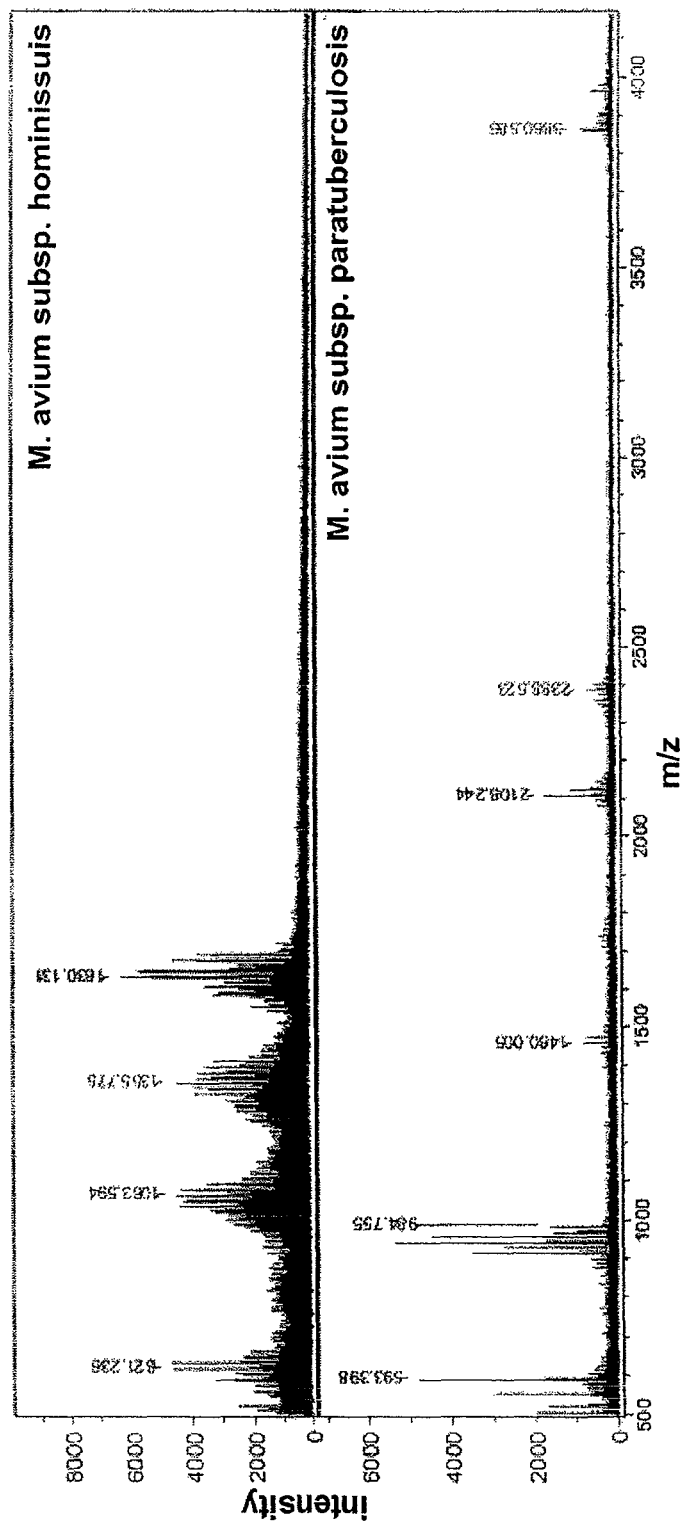
FIG. 6 shows matrix-assisted laser desorption ionization time-of-flight mass spectra of total bacterial lipids of *Mycobacterium avium* subspecies *hominissuis* (top); and *Mycobacterium avium* subspecies *paratuberculosis* (bottom).

FIG. 6 shows MALDI-TOF mass spectra of total bacterial lipids of *Mycobacterium avium* subspecies *hominissuis* (top); and *Mycobacterium avium* subspecies *paratuberculosis* (bottom). The two bacterial subspecies can clearly be identified using the mass spectra thereof.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for identifying a single bacterial subspecies containing at least one extractable lipid, comprising the steps of:
    extracting said at least one bacterial lipid using an organic solvent; and
    identifying said at least one lipid by its molecular weight, wherein the presence of the lipopeptide Para-LP-01 confirms the presence of *Mycobacterium avium* subspecies paratuberculosis.

* * * * *